United States Patent [19]

Landry et al.

[11] Patent Number: 5,108,693
[45] Date of Patent: Apr. 28, 1992

[54] NON-DESTRUCTIVE DIMENSIONAL AND FLAW INSPECTION OF THIN WALL TUBE WELDMENTS

[75] Inventors: James D. Landry; Mark A. Joyce, both of Wilmington, N.C.; John D. Young, Rexford; Robert S. Gilmore, Burnt Hills, both of N.Y.; Frederick C. Schoenig, Jr., Wilmington, N.C.

[73] Assignee: General Electric Company, San Jose, Calif.

[21] Appl. No.: 250,187

[22] Filed: Sep. 28, 1988

[51] Int. Cl.⁵ .............................................. G21C 17/00
[52] U.S. Cl. .................................. 376/245; 376/252; 73/637
[58] Field of Search ............... 376/245, 252, 260, 261; 73/637, 638, 622

[56] References Cited

U.S. PATENT DOCUMENTS

| | | | |
|---|---|---|---|
| 3,169,393 | 2/1965 | Stebbins | 73/622 |
| 3,570,279 | 3/1971 | Davies | 73/626 |
| 4,065,960 | 1/1978 | Grabendorfer et al. | 73/627 |
| 4,098,130 | 7/1978 | Coffey et al. | 73/614 |
| 4,213,345 | 7/1980 | Dufour | 73/637 |
| 4,217,782 | 8/1980 | Pont | 73/637 |
| 4,393,711 | 7/1983 | Lapides | 73/592 |
| 4,424,235 | 1/1984 | Sugiyama | 73/579 |
| 4,428,237 | 1/1984 | Zeger et al. | 73/592 |
| 4,541,064 | 9/1985 | Livingston | 73/637 |
| 4,554,128 | 11/1985 | Parker et al. | 376/252 |
| 4,660,419 | 4/1987 | Derkacs et al. | 73/622 |
| 4,665,734 | 5/1987 | Joet | 73/637 |
| 4,857,260 | 8/1989 | Schoenig, Jr. et al. | 376/245 |

FOREIGN PATENT DOCUMENTS 6066 12/1979 European Pat. Off.

*Primary Examiner*—Daniel D. Wasil
*Attorney, Agent, or Firm*—Robert R. Schroeder

[57] ABSTRACT

Nuclear fuel cladding tube end plug welds are ultrasonically scanned to develop data indicative of weld thickness, weld penetration, and the existence and size of any included feature, such as pores. A computer analyzes the data to determine critical weld characteristics which are then tested against established quality assurance standards to see if the end plug weld is acceptable, all on an automated production line basis.

15 Claims, 7 Drawing Sheets

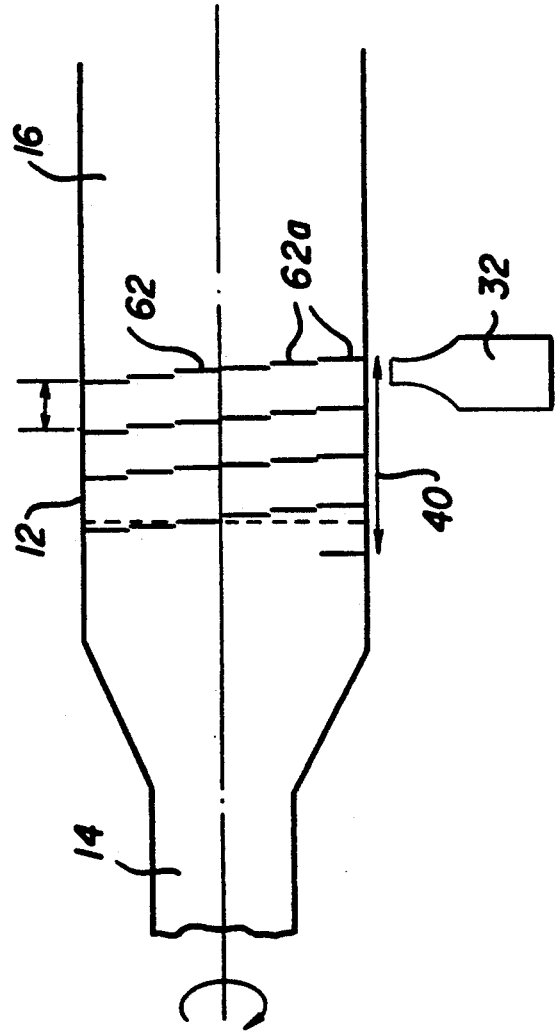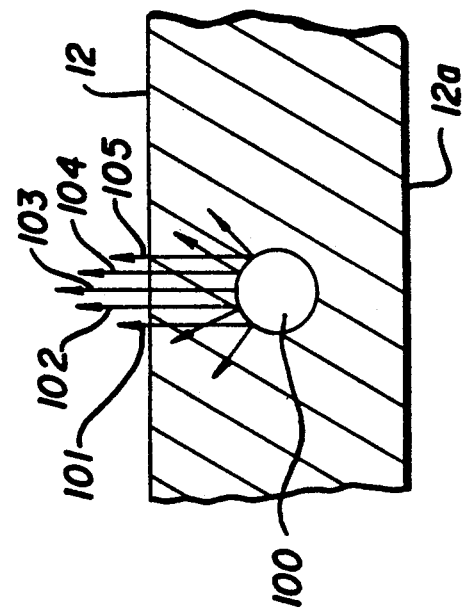

NON-DESTRUCTIVE DIMENSIONAL AND FLAW INSPECTION OF THIN WALL TUBE WELDMENTS

The present invention relates to a non-destructive inspection method for performing quality assurance examinations of tube welds and to apparatus for performing same.

BACKGROUND OF THE INVENTION

In certain applications, the integrity of a part weldment is of critical importance to assure against future service failures. One such example is a nuclear fuel rod which is comprised of a column of fuel pellets contained in an elongated cladding tube formed of a zirconium alloy. End plugs, also of a zirconium alloy, are welded to the open ends of the tube to seal the pellet column therein. These end plug welds must meet exacting standards of integrity if they are to withstand the high internal pressures developed over the fuel rod life. Heretofore, the head end plug weld has been effected as a bead weld, and thus visual inspection was adequate to verify the presence of sufficient weld cross section to withstand the high internal pressures. Random end plug weld samples were examined using X-ray radiography at several viewing angles. The resulting radiographs had to be visually examined, and porosities were detectable and measurable only if located in the several view planes. Porosity resolution was limited to pores in excess of a five mil diameter. Other end plug weld samples were destructively examined by metallographic sectioning mainly for the purpose of qualifying the welding process and detecting process excursion.

Recent improvements in bundle spacer designs require that the head end plug weld be a flush weld. Visual inspection of flush welds is not an adequate quality assurance test of weld integrity. That is, absent the weld bead, visual inspection can not determine that the weld is continuous and of a cross sectional area at least equal to that of the cladding tube. Consequently, non-destructive examination of the weld internal characteristics is necessary to determine if a flush weld meets the requisite quality assurance standards for integrity. In view of the criticality of this end plug weld, each and every one must be examined.

In the commonly assigned, copending application entitled "Apparatus for Assembling and Welding End Plugs to Nuclear Fuel Cladding Tubes and Inspecting the End Plug Welds on an Automated Basis, Ser. No. 07/250,059, there is disclosed and claimed apparatus for welding a head end plug to the open ends of a succession of cladding tubes and then ultrasonically inspecting each end plug weld on an automated, production line basis. To expedite production, this ultrasonic inspection must be performed in timely fashion consistent with the time required to mate an end plug with the tube open end and weld them together. This inspection must include measuring the tube wall thickness adjacent the weld, detecting the presence and size of any flaws in the weld, determining the minimum weld net cross sectional area of the weld, and the extent of weld penetration into the tube open end. These determinations must then be tested against strict quality assurance standards to decide whether the end plug weld is acceptable or rejectable. All of this should be accomplished in a short period of time, e.g., less than thirty seconds, without human intervention in order that quality assurance inspection not pose a production bottleneck.

It is accordingly an object of the present invention to provide an improved method for non-destructively examining the characteristics of weldments.

A further object is to provide a method of the above-character for non-destructively examining the dimensional and internal characteristics of weldments.

An additional object is to provide a method of the above-character, wherein the ultrasonic echos are converted to inspection data indicative of the weldment characteristics for comparison against quality assurance standards pursuant to determining on an automated basis whether a weldment is acceptable or rejectable.

A still further object is to provide a method of the above-character for non-destructively examining the integrity of the weld uniting an end plug to an open end of a nuclear fuel cladding tube on automated production line basis.

Yet another object is to provide ultrasonic inspection apparatus for practicing the method of the above-noted character.

Other objects of the invention will in part be obvious an in part appear hereinafter.

SUMMARY OF THE INVENTION

In accordance with the present invention there is provided a quality assurance method and apparatus for conducting dimensional and flaw inspection of weldments on an automated basis. The invention is disclosed in its application to the quality assurance inspection of nuclear fuel cladding tube end plug welds, wherein the end plug welded end of a tube is axially inserted into an ultrasonic inspection station. The tube is clamped in a reference position and then rotated while an ultrasonic transducer is translated in a direction parallel to the tube axis to scan the end plug weld in a tightly spiralled scanning pattern. The ultrasonic transducer is pulsed at a multiplicity of uniformly angularly spaced data points along each helical scan line of the scanning pattern. The echos received at each data point are variously detected to develop tube and weld thickness data, amplitude data indicative of internal features, such as pores, and feature depth data.

These data are accummulated on a data point basis in a data acquisition system over the entire scanning pattern and then analyzed by a computer to identify from amplitude data those data points which are common to each separate feature. The maximum amplitude data for each feature is normalized using the associated feature depth data to develop a rather accurate indicator of feature size. Each feature normalized maximum amplitude data is tested against a threshold limit, and the weld is rejected if this limit is exceeded. The cross sectional area of the features included in the weld cross section slice represented by each scan line is calculated. The thickness data is then analyzed to find the minimum weld thickness and to reject the weld if a minimum thickness threshold limit is not exceeded. From the thickness data, the weld gross cross sectional area of each scan line slice is computed. The cross sectional areas of those features included in each slice are substracted from its computed gross cross sectional area to calculate net cross sectional area. The minimum slice net cross sectional area is tested against a threshold limit, and the weld is rejected if this limit is not exceeded. The thickness data is further analyzed to determine the degree to which the weld has penetrated the tube open. Insufficient weld penetration is yet another basis for weld rejection.

The invention accordingly comprises the features of construction, combination of elements, and arrangement of parts, in addition to the method of operating same, all as will be exemplified in the description hereinafter set forth, and the scope of the invention will be indicated in the claims.

For a fuller understanding of the nature and objects of the invention, reference may be made to the following detailed description taken in conjunction with the accompanying drawings, in which:

FIG. 2 is an enlarged, fragmentary side view illustrating the ultrasonic sanning pattern utilized to examine an end plug weld;

FIG. 6 is a fragmentary sectional view of an end plug weld with an included pore;

Corresponding reference numerals refer to like parts throughout the several views of the drawings.

DETAILED DESCRIPTION

Figure 1:
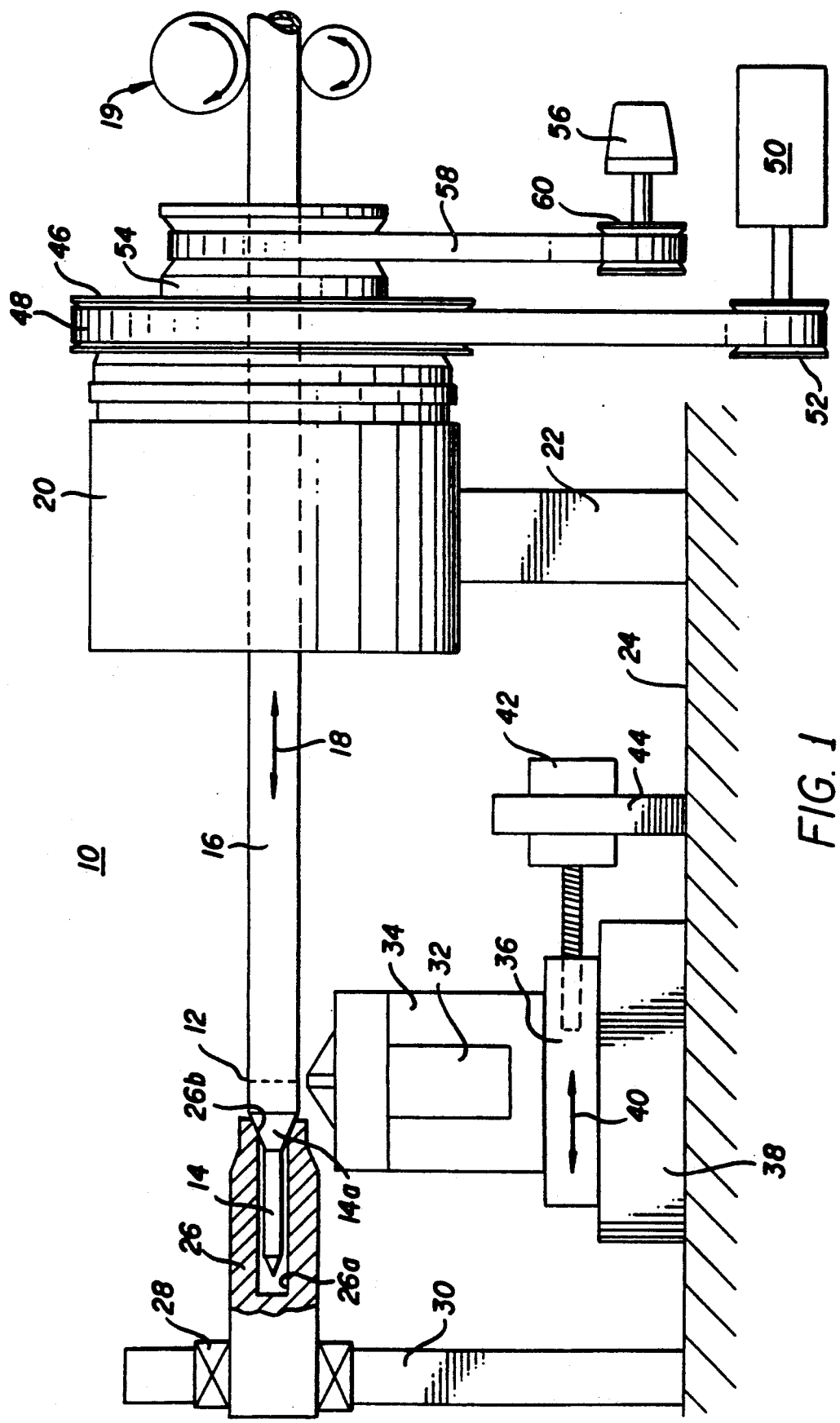
FIG. 1 is a side view, partially in schematic form, of an ultrasonic inspection station for examining the weld joining an end plug to the open end of a nuclear fuel cladding tube.

Referring to FIG. 1, a weld inspection station, generally indicated at 10, is utilized to inspect the integrity of a weld 12 affixing an end plug 14 to the open end of a nuclear fuel cladding tube 16. The tube is formed of a suitable metal, such as a zirconium alloy, in lengths typically in excess of ten feet, with an inner diameter on the order of 400 mils and a typical wall thickness of 30 mils. The end plug is normally formed of the same metal as the tube. The tube is axially propelled, as indicated by arrow 18, end plug end first, into inspection station 10 by suitable means, such as a pinch wheel drive 19. Entry into the inspection station is through the central opening of an air chuck 20 supported by a stand 22 from a table 24. An inspection reference position is established by a live centering stop 26 rotatably mounted by bearings 28 carried by a table supported stand 30. This stop is formed with an axial bore 26a having a chamferred entry surface 26b against which the conical surface 14a of the end plug abuts to halt tube insertion precisely at the inspection reference position. Air chuck 20 is then activated to clamp the tube thereat. With the tube so positioned in the inspection station, end plug weld 12 is vertically aligned with the underlying tip of an ultrasonic transducer 32. This transducer is incorporated with a water bubbler 34 adapted to provide a continuing supply of couplant fluid for weld-probing ultrasonic energy periodically generated thereby. The bubbler is carried by a base 36 which is mounted by a table-supported slide 38 for movement in a direction parallel to the tube axis, as indicated by arrow 40. This weld scanning ultrasonic transducer movement is produced by a precision stepping motor 42 mounted to table 24 by a stand 44.

Air chuck 20 is equipped with a pulley 46 which is engaged by a timing belt 48 driven by a motor 50 via a drive pulley 52. A second pulley 54, affixed to pulley 46, drives an angular position encoder 56 via interconnecting timing belt 58 and pulley 60.

From the description thus far, it is seen that, with tube 16 clamped in air chuck 20, energization of motor 50 is effective to rotate the tube, while encoder provides a continuous indication of the tube angular position relative to ultrasonic transducer 32. During tube rotation, motor 42 is periodically stepped under the control of encoder 56 to index ultrasonic transducer 32 in a direction parallel to the tube axis over the length of end plug weld 12. There is thus generated a spiralled weld scanning pattern which is illustrated in FIG. 2. Each essentially helical scan line 62 of this pattern is comprised of a plurality axially staggered, short circumferential segments 62a created during concurrent tube rotation and periodic stepping of motor 42. In a practically embodiment of the present invention, each full circumference helical scan line 62 is comprised of eighteen segments 62a, and the pitch of the spiral scan pattern or axial separation between scan lines is two mils.

Figure 3:
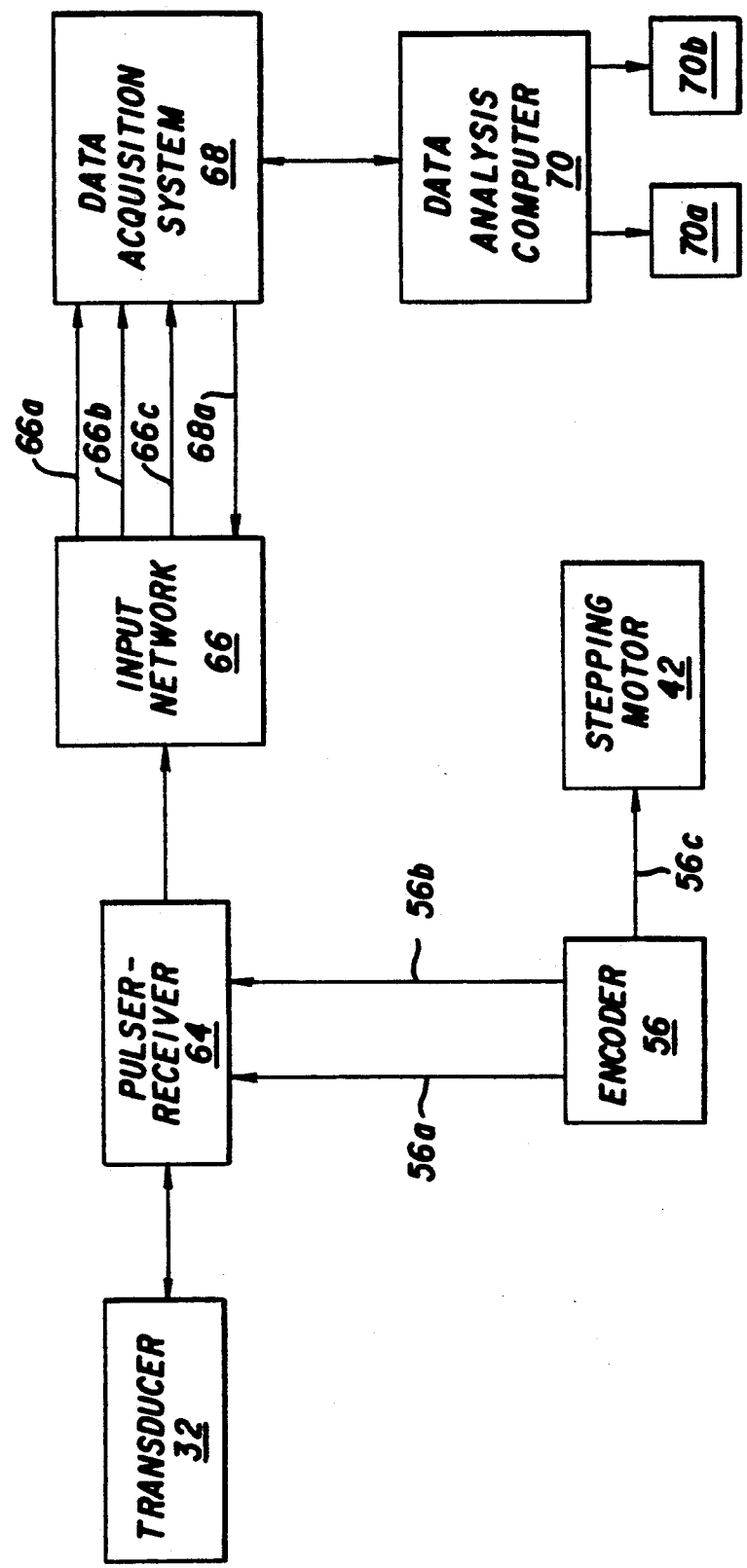
FIG. 3 is a block diagram of a circuit for processing the end plug weld inspection data obtained from the inspection station of FIG. 1.

Referring to the block diagram of FIG. 3, a pulser-receiver 64 pulses ultrasonic transducer to generate a burst of ultrasonic weld probing energy in in response to a timing pulse over lead 56a generated by encoder 56 at a zero degree reference angular position during each revolution of tube 16. Pulser also pulses the transducer in response to a multiplicity encoder timing pulses issued over lead 56b at uniformly spaced angular increments referenced to this zero degree position during each tube revolution. Encoder pulses generated over lead 56c control stepping motor 42 to index the transducer incrementally over the weld axial length, i.e., from scan segment 62a to scan segment (FIG. 2). The ultrasonic echos sensed by transducer 32 incident to each burst of probing energy are received by pulser-receiver 64 and supplied to an input network 66 where they are variously detected to develop tube and weld thickness data on lead 66a, amplitude data on lead 66b, and depth data on lead 66c to a data acquisition system 68. The amplitude data is indicative of the the existence and size of any internal feature, e.g., pore, included in the weld cross section and the depth data is indicative of the depth of the feature measured from the weld outer surface. These three sets of data are accummulated in the data acquisition system, which may be a Digital Equipment Corporation PDP 11/73, on a data point basis correlated to position of the transducer relative to the weld at the instant of each probing energy burst. The transducer may be a Panametrics V3425 operated at a frequency of fifty megaHertz with a focal length of 0.5 inches and an aperture in the range of 0.19 to 0.25 inches.

After all the data for the full weld scanning pattern, which may consist of 120 helical scan lines 62 (FIG. 2), have been accummulated in the data acquisition system, a data analysis computer 70 analyzes the data to determine if the end plug weld is acceptable from a quality assurance standpoint. This computer, which may be a Digital Equipment Corporation VAX Station II/GPX, is equipped with various peripherals including, inter alia, a color graphics printer-plotter 70a and color monitor 70b. With the transfer of each data set for each data point to data acquisition system 68, input network 66 is reset over lead 68a so that it is conditioned to the develop the data set for the next data points. Transducer is pulsed at a rate to establish, for example, 750 data points along each helical scan line 62. Preferably, the circumferential spacing between data points is the same as the spacing between helical scan lines, e.g., two mils.

Figure 4:
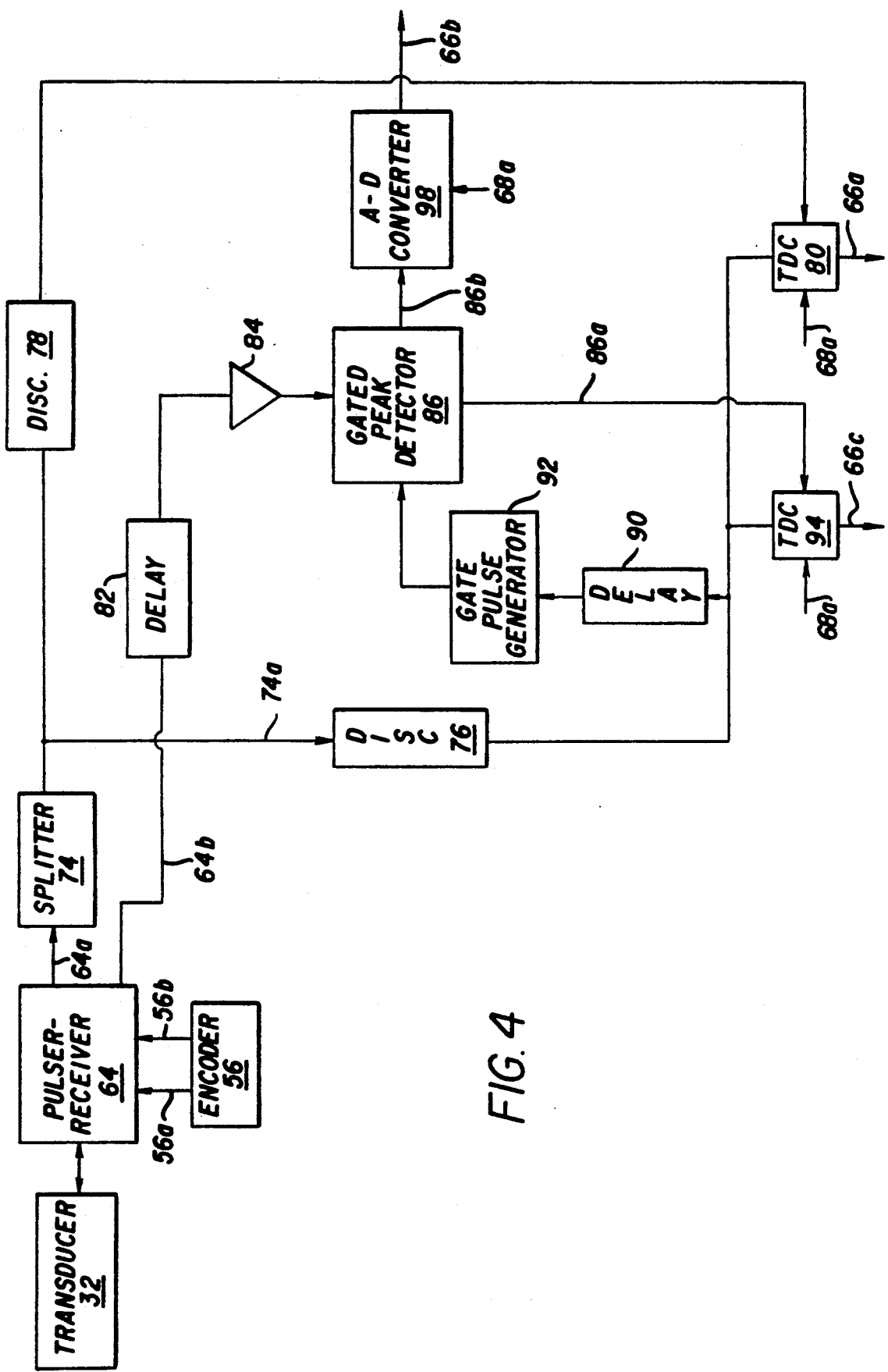
FIG. 4 is a circuit block diagram illustrating details of the input network seen in FIG. 3.
Figure 5:
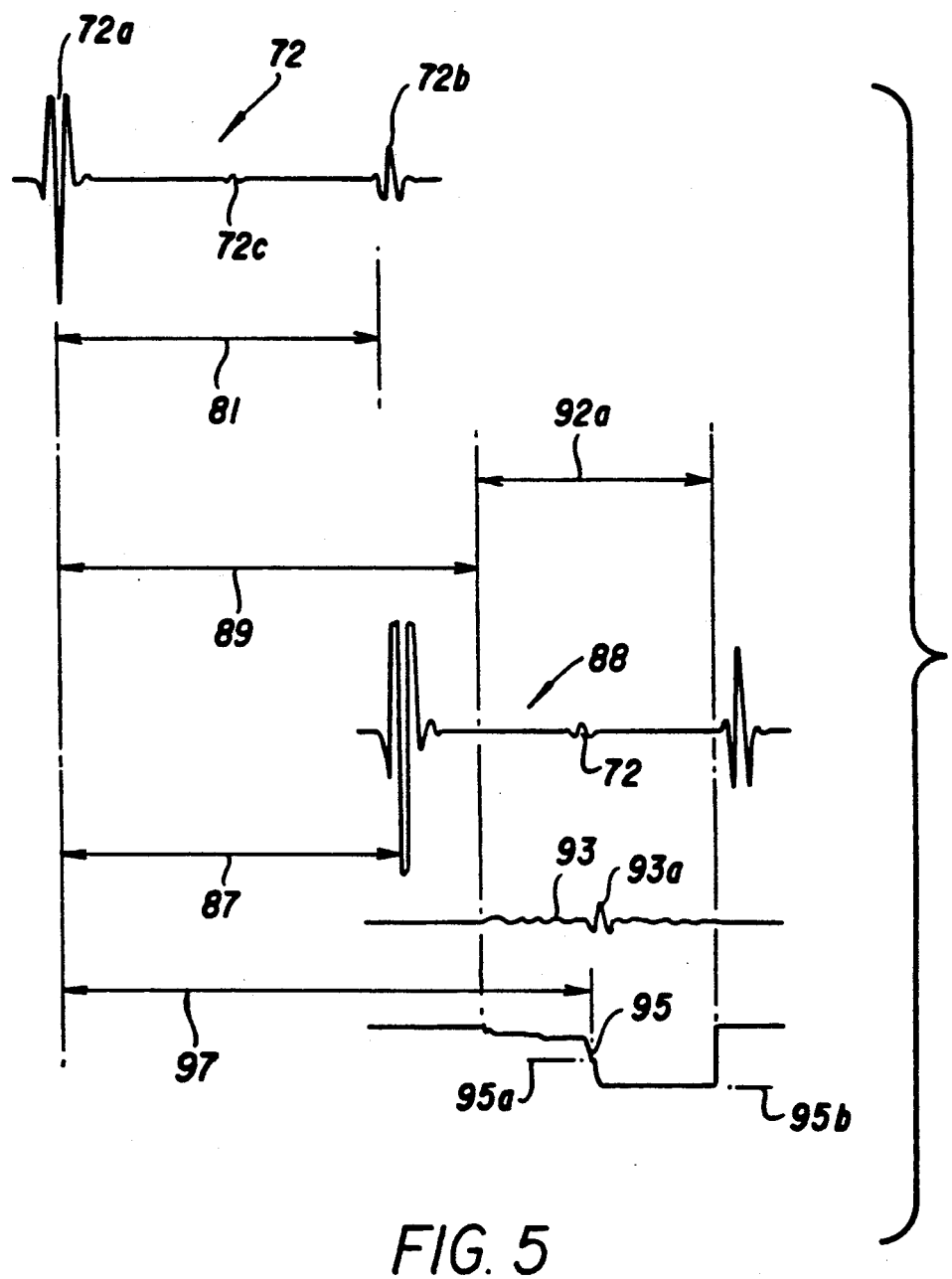
FIG. 5 is a signal timing diagram illustrating the opeation of the input network of FIG. 4.

Turning to FIG. 4, upon receipt of each timing pulse from encoder 56, the pulser section of pulser-receiver 64 drives transducer 32 with a "main bang" pulse to generate a burst of weld probing energy. The receiver section establishes in response to this main bang pulse a window or gate defining a time interval during which echos sensed by the transducer are recognized. These echos are in the form of a gated RF signal indicated at 72 in FIG. 5, which includes a relatively high amplitude ripple 72a indicative of the echo reflected from the outer surface of the end plug weld 12 and a subsequent lower amplitude ripple 72b indicative of the echo reflected from the inner weld surface. If a feature such as a pore exists in the weld cross section underlying the particular data point being probed, the echo therefrom is indicated as a still lower amplitude ripple 72c variously positioned in time between ripples 72a, 72b depending on the feature depth.

Returning to FIG. 4, this gated RF signal is fed over lead 64a to a splitter 74 which provides duplicates thereof on output lead 74a to a first discriminator 76 and on lead 74b to a second discriminator 78. Discriminator 76 is designed to detect outer surface echo ripple 72a and, upon doing so, signals a time-to-digital signal converter over lead 76a to start counting clock pulses. Discriminator 78, on the other hand, is designed to detect inner surface echo 72b and to then signal converter 80 over lead 78a to stop counting clock pulses. The accumulated count in this converter is indicative of the thickness of the weld cross section underlying the probed data point and constitutes thickness data fed to data acquisition system 68 over lead 66a. Weld thickness is illustrated graphically at 81 in FIG. 5.

Still referring to FIG. 4, ungated RF echo signal 72 on lead 64b from the receiver section of pulser-receiver 64 is delayed by a delay line 82, amplified by an amplifier 84 and supplied to a gated peak detector 86. This delayed and amplified signal is indicated at 88 in FIG. 5, with the delay imposed by delay line 82 illustrated graphically at 87. The signal on lead 76a issued by discriminator 76 upon detection of outer surface ripple 72a is delayed by a delay line 90 (graphically illustrated at 89) and then utilized to trigger a gate generator 92 to generate an inspection window (graphically illustrated at 92a). The RF signal within this inspection window is further amplified in the gated peak detector, as indicated at 93. Meanwhile, the signal on line 76a issued by discriminator 76 in response to the outer surface echo to start converter 80 to count clock pulses also starts an identical converter 94 to count the same clock pulses. The DC level of the gated peak detector output indicated at 95, tracks the peak amplitude of any amplified feature echo RF signal 93a within inspection window 92a. When this output signal exceeds a predetermined threshold level, indicated at 95a, gated peak detector 86 issues a signal on lead 86a to halt the count of clock pulses in converter 94. The count, proportional to time interval 97, held in this converter is communicated to the data acquisition system over lead 66c where a count proportional to the delay 87 impose by delay line 82 is subtracted out to provide a net count indicative of feature depth.

When the inspection window 92a is closed by gate generator 92, the gated peak detector DC output is sitting at a level 95b proportional to the maximum peak amplitude of any feature echo RF ripple 93a detected within the inspection window. This maximum peak amplitude is applied via lead 86b to an analog-to-digital converter 98 where it is converted to feature amplitude data and communicated on demand to the data acquisition system over lead 66b. Upon receipt of the complete set of weld thickness, feature amplitude and feature depth data for one data point, the data acquisition system resets converters 80, 94 and 98 to zero to ready input network 66 to detect the RF echo signal for the next data point.

To appreciate the significance of feature amplitude data, reference is made to FIG. 6, wherein a typcial internal feature in the form of a pore 100 is illustrated. Pores are invariable in shape of spherical voids. Arrows 101-105 represent ultrasonic probing of an end plug weld 12 at five consecutive data points along a helical scan line 62 (FIG. 2). When an ultrasonic energy probing encounters the metal-gas interface at the pore upper boundary, it is reflected. It will be appreciated that maximum energy reflection back to the transducer occurs for probing 103 which is incident at the top center of the pore boundary. Here the incident angle of the metal-gas interface is most normal to the probing energy. As the pore size increases, so does its radius of curvature, and thus the top center incident angle becomes more normal to an energy probing thereat. Thus, the maximum amplitude feature echo sensed by the transducer can be reliable indicator of pore size. As seen from FIG. 6, energy probings 101, 102, 104 and 105 to either side of probing 103 encounter increasing incident angles at the metal-gas interface. Thus, less probing energy is reflected back to the transducer for probings 102 and 104, and lesser still for probings 101 and 105. Since ultrasonic probing energy does not propagate through voids, such as a pore 100, little energy reflection is observed from the underlying inner surface 12a of the weld. Thus, weld thickness data at pore data point locations is typically unavailable.

At the conclusion of a weld scanning pattern, which may involve 120 or more helical scan lines 62 (FIG. 2), a set of weld thickness, feature amplitude and feature depth data has been accummulated for each and every data point in data acquisition system 68 (FIG. 3). Computer 70 then begins its data analysis in accordance with a program illustrated in the flow chart of FIG. 7. Those data points having feature amplitude data exceeding a predetermined minimum threshold are identified as feature-indicating data points (FIDP), as represented by block 110. The computer then assembles those FIDP data points that are contiguously located to one another, i.e. touching each other, into exclusive, identifiable data point feature groups (DPFG), as represented by block 112. As represented by block 114, computer 70 finds the maximum feature amplitude data for each feature group DPFG and computes its maximum normalized amplitude (MNA). This normalization computation involves correcting each maximum feature amplitude data for temperature variations in the couplant fluid (bubbler 34, FIG. 1) and the feature depth at the data point of maximum feature amplitude. Temperature correction accounts for transducer focus and sensitivity changes due to couplant temperature variations. Feature depth correction utilizes calibration factors empirically determined from the ultrasonic examination of standard end plug welds containing features of known sizes and depths.

As represented by block 116, the maximum normalized amplitude (MNA) for each identified feature (DPFG) is tested against a quality assurance, threshold, and the end plug weld is rejected if this limit is exceeded, i.e., the feature is unacceptably large. For each scan line, the computer then separately counts the number of feature-indicating data points FIDP included in each feature (block 118). In FIG. 6, this count could include the five data points of probings 101-105. From this count and knowing the data point spacing, the diameter X of each of the separate features in each scan line is computed. This diameter is then squared ($X^2$) in each case to provide a measure of the cross sectional area of each feature included in each of the multiple transverse slices of the end plug weld respectively associated with the plural scan lines. Since pores are spherical in shape, squaring their diameters provides a rather accurate indication of their cross sectonal areas included in each transverse slice.

The thickness data for each data point is normalized using an empirically developed calibration factor and checked to find the minimum weld thickness (block 120). Data point thickness data which is unavailable due to the presence of features are assigned thickness data comparable to that of the data points just beyond the features. The end plug weld is rejected if the minimum weld thickness is less than a quality assurance established minimum limit (block 122). As represented by block 124, the normalized thickness data for the data points of each scan lines are added together to produce a total which is proportional to the gross cross sectional area of the included transverse slice. The computed gross cross sectional area of each slice is then reduced by the computed feature cross sectional $X^2$ of those features included in the respective slices (block 118) to derive a net weld cross sectional area (A) for each slice (scan line), as represented by block 126. If the minimum net cross sectional area of any slice is less than a predetermined threshold limit, the weld is rejected (block 128).

Figure 8:
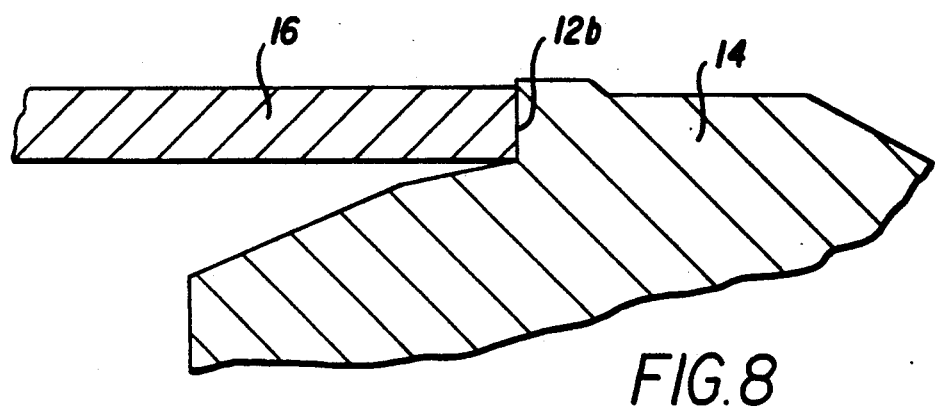
FIG. 8 is a fragmentary sectional view illustrating the mated relationship of a tube and an end plug prior to welding.
Figure 9:
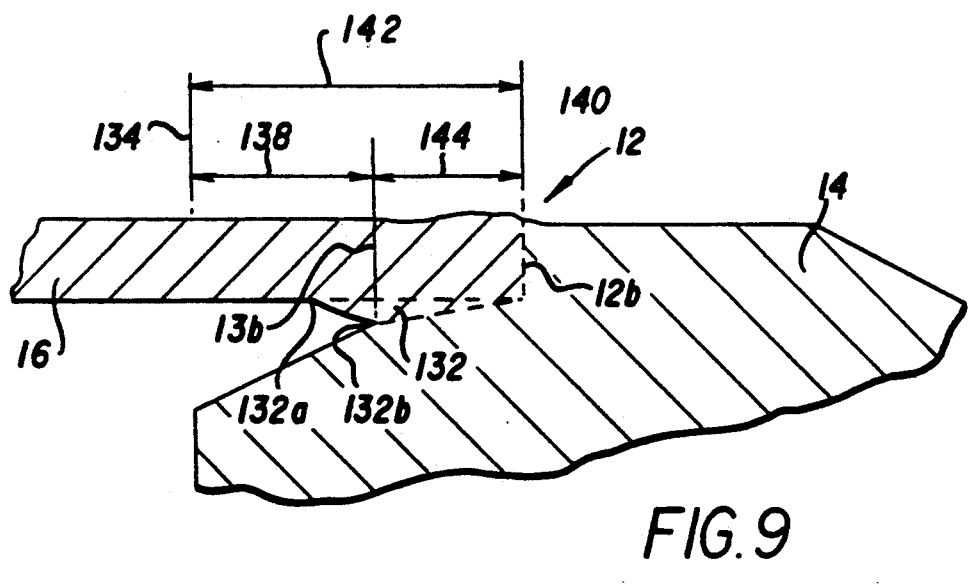
FIG. 9 is a fragmentary sectional view illustrating a typical end plug weld.

The final end plug weld quality assurance check is to determine the extent of weld penetration into the open end of tube 16, as represented by block 130. FIG. 8 illustrates in cross section the mated relationship of tube 16 and end plug 14 preparatory to welding. The original seam between these parts is indicated at 12b. FIG. 9 illustrates in cross section an acceptable degree of weld penetration in that weld nugget 132 is seen to penetrate the tube open end well inwardly from seam 12b. Since end plug weld 12 is always precisely positioned in the inspection station 10 by line centering stop 26 (FIG. 1) the position of seam 12b in the ultrasonic scanning pattern is known. Scanning begins over the unweld portion of the tube inwardly from nugget 132, as indicated at 134. As scanning progress from helical scan line to helical scan line, thickness data is obtained up to the point 136 where the exposed nugget surface merges with the end plug surface. Thereafter, any echoes reflected from the far outer surface of the weld are well outside the inspection gate of pulser-receiver 64 (FIG. 3). The number of scan lines, represented by the axial dimension 138 in FIG. 9, to reach the first full scan line whose data points are all devoid of thickness data (point 136) is substracted from the known number of scan lines to reach point 140 aligned with seam 12b, represented by the axial dimensiom 142, yields a number indicative of weld penetration, represented by dimension 144. If this number is less than a quality assurance-established minimum, the end plug weld is rejected (block 146).

Figure 7:
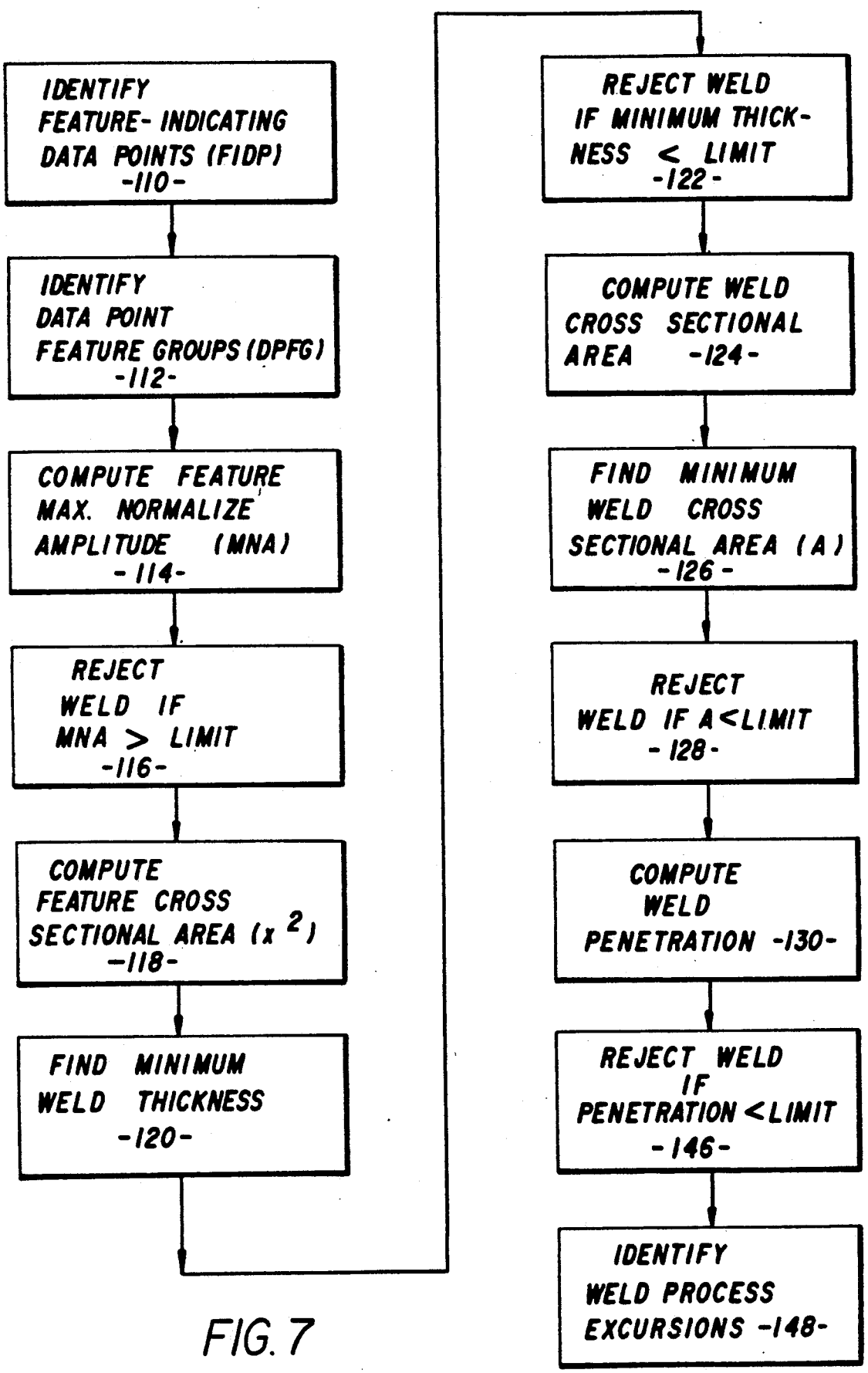
FIG. 7 is a flow chart illustrating the programmed operation of the data analysis computer in FIG. 3.

Block 148 in the flow chart of FIG. 7 indicates that the thickness data is also analyzed for possible welding process excursions. The volume of weld nugget 132 is calculated, and the uniformity of nugget cross sectional area in both transverse and axial planes is examined. The uniformities of the nugget edges 132a, and 132b around their circumferences are also examined. Information developed from these examinations is utilized to monitor weld geometric characteristics and to alert personnel that welding proccess parameters may require adjustments should these characteristics show a trend away from acceptable standards. Alternatively, this information may be utilized to automatically effect feedback control of the welding process parameters.

It will be appreciated that the sequence of operations illustrated in FIG. 7 is merely illustrative, and thus, in practice, the various quality assurance checks may be performed in a variety of different orders.

In addition to rendering end plug weld accept/reject decision on an automated, production line basis, the data analysis may, particularly in the case of rejected welds, be programmed to display the weld examination data on color monitor 70b in the form of a graph with the axially spaced scan lines plotted along one axis and the circumferentially spaced data points of each scan line plotted along the other axis. Thickness data are indicated by variations in color. Included features are displayed as blanked pixels. A hard copy of this graph is generated by printer-plotter 70a. The computer also has all the data necessary to generate graphs for display and printing of the tube and weld thickness for any selected radial or axial slice through the weld.

It is seen from the foregoing description that the objects set forth above, including those made apparent herein, are efficiently attained, and since certain changes may be made in the disclosed embodiment without departing from the invention, it is intended that all matters contained herein be taken as illustrative and not in a limiting sense.

Having described the invention, what is claimed as new and desired to secure by Letters Patent is:

1. A method of non-destructively examining a weld section of a thin walled tube comprising the steps of:
   A. locating the weld section at an axial reference position;
   B. rotating the tube;
   C. translating an ultrasonic transducer along a path parallel to the axis of the rotating tube to execute a predetermined scanning pattern consisting of a multiplicity of axially spaced, circumferential scan lines encompassing the weld section,
   D. pulsing the transducer to emit ultrasonic weld section-probing energy at a multiplicity of data points distributed along the scan lines throughout the scanning pattern;
   E. developing echo signals from the reflections of ultrasonic probing energy at each data point;
   F. detecting said echo signals to derive thickness data indicative of the weld section thickness at each data point and amplitude data indicative of the presence of a feature included in the weld section at each data point;

G. assembling those data points having amplitude data exceeding a predetermined threshold into distinct feature groups of mutually adjacent data points;

H. identify the data point in each feature group having the maximum magnitude amplitude data; and I. testing the maximum magnitude amplitude data of each feature group against a first quality assurance threshold limit to determine if the weld section is acceptable.

2. The method defined in claim 1, which further includes the steps of analyzing the thickness data of all data points to find the minimum weld section thickness, and testing the minimum weld section thickness against a second quality assurance threshold limit to determine if the weld section is acceptable.

3. The method defined in claim 1, which further includes the steps of detecting the echo signals to derive depth data indicative of the depth of an included feature relative to a surface of the weld section for all data points having amplitude data, and correcting the maximum magnitude amplitude data for each feature using the depth data of the same data point to develop a single normalized maximum magnitude amplitude data for each included feature for testing against the first quality assurance threshold limit.

4. The method defined in claim 3, which further includes the steps of providing couplant fluid intermediate the transducer and the weld section surface, monitoring the couplant fluid temperature, and further correcting the maximum magnitude amplitude data of each feature for variations in couplant fluid temperature.

5. The method defined in claim 1, which further includes the steps of determining a dimension of each feature by counting the number of data points in the feature group thereof along each scan line, and squaring each determined feature dimension to calculate each feature cross sectional area included in each scan line.

6. The method defined in claim 5, which further includes the steps of separately summing the thickness data for those data points included in each scan line to calculate the weld section gross cross sectional area encompassed by each scan line, subtracting the feature cross sectional area from the weld section gross cross sectional area to calculate the weld section net cross sectional area for each scan line, and testing the weld section minimum net cross sectional area against a second quality assurance threshold limit to determine if the weld section is acceptable.

7. The method defined in claim 6, which further includes the step of using for those data points lacking valid thickness data the valid thickness data of the most contiguous data points in the calculation of the weld section gross cross sectional area encompassed by each scan line.

8. The method defined in claim 1, wherein the weld section joins an end plug to one open end of the tube, said method further including the steps of starting the first scan line of the scanning pattern along the unwelded portion of the tube a known distance from the original open end of the tube, identifying the first subsequent scan line whose data points exhibit an absence of thickness data, calculating from known position in the scanning pattern of the identified scan line the extent of weld penetration into the tube open end, and testing the calculated weld penetration against a second quality assurance threshold limit to determine if the end plug weld is acceptable.

9. The method defined in claim 8, which further includes the steps of analyzing the thickness data of all data points to find the minimum weld section thickness, and testing the minimum weld section thickness against a third quality assurance threshold limit to determine if the weld section is acceptable.

10. The method defined in claim 8, which further includes the steps of detecting the echo signals to derive depth data indicative of the depth of an included feature relative to a surface of the weld section for all data points having amplitude data, and correcting the maximum magnitude amplitude data for each feature using the depth data of the same data point to develop a signal normalized maximum magnitude amplitude data for each included feature for testing against the first quality assurance threshold limit.

11. The method defined in claim 10, which further includes the steps of providing couplant fluid intermediate the transducer and the weld section surface, monitoring the couplant fluid temperature, and further correcting the maximum magnitude amplitude data of each feature for variations in couplant fluid temperature.

12. The method defined in claim 8, which further includes the steps of determining a dimension of each feature by counting the number of data points in the feature group thereof along each scan line, and squaring each determined feature dimension to calculate each feature cross sectional area included in each scan line.

13. The method defined in claim 12, which further includes the steps of separating summing the thickness data for those data points included in each scan line to calculate the weld section gross cross sectional area encompassed by each scan line, substracting the feature cross sectional area from the weld section gross cross sectional area to calculate the weld section net cross sectional area for each scan line, and testing the weld section minimum net cross sectional area against a second quality assurance threshold limit to determine if the weld section is acceptable.

14. The method defined in claim 13, which further includes the step of using for those data points lacking valid thickness data the valid thickness data of the most contiguous data points in the calculation of the weld section gross cross sectional area encompassed by each scan line.

15. The method defined in claim 13, which further includes the step of analyzing the thickness data to identify welding process excursions.

* * * * *